(12) United States Patent
Murphy (10) Patent No.: US 12,417,841 B2
(45) Date of Patent: Sep. 16, 2025

(54) PATIENT MONITORING

(71) Applicant: KONINKLIJKE PHILIPS N.V., Eindhoven (NL)

(72) Inventor: Graham Murphy, Ashwood Way (GB)

(73) Assignee: Remote Diagnostic Technologies Limited, Basingstoke (GB)

( * ) Notice: Subject to any disclaimer, the term of this patent is extended or adjusted under 35 U.S.C. 154(b) by 1102 days.

(21) Appl. No.: 16/620,268

(22) PCT Filed: Jun. 27, 2018

(86) PCT No.: PCT/GB2018/051798
§ 371 (c)(1),
(2) Date: Dec. 6, 2019

(87) PCT Pub. No.: WO2019/002859
PCT Pub. Date: Jan. 3, 2019

(65) Prior Publication Data
US 2021/0090729 A1    Mar. 25, 2021

(30) Foreign Application Priority Data
Jun. 28, 2017 (GB) .................................. 1710360

(51) Int. Cl.
*G08G 1/123* (2006.01)
*A61B 5/00* (2006.01)
(Continued)

(52) U.S. Cl.
CPC .......... *G16H 40/67* (2018.01); *A61B 5/0022* (2013.01); *A61B 5/6893* (2013.01);
(Continued)

(58) Field of Classification Search
CPC ........ G16H 40/67; G16H 10/60; G16H 40/20; H04W 4/48; H04W 4/029; A61B 5/0022;
(Continued)

(56) References Cited

U.S. PATENT DOCUMENTS 5,375,604 A * 12/1994 Kelly ..................... A61B 5/332
600/483
6,183,417 B1 * 2/2001 Geheb ..................... G16Z 99/00
600/301
(Continued)

FOREIGN PATENT DOCUMENTS

GB    1208654 A    10/1970
JP    2011029898 A    2/2011
(Continued)

OTHER PUBLICATIONS

Al-Qura et al., IoT-Based Ambulatory Vital Signs Data Transfer System (Year: 2018).*
(Continued)

*Primary Examiner* — Quang Pham (57) ABSTRACT

An apparatus for medically monitoring a patient comprises at least one input to receive medical data relating to or received from a patient being monitored and memory to store the received medical data and a received vehicle identifier, which is associated with a vehicle. The apparatus further comprises a communications module and a processor. The processor may be configured to generate patient data, associated with the patient being monitored, comprising the medical data and the vehicle identifier. The processor may also be configured to control the communications module to transmit the patient data to a remote server.

31 Claims, 5 Drawing Sheets

(51) Int. Cl.
| | |
|---|---|
| *B60R 16/023* | (2006.01) |
| *G16H 10/60* | (2018.01) |
| *G16H 40/67* | (2018.01) |
| *H04L 67/12* | (2022.01) |
| *H04W 4/029* | (2018.01) |
| *H04W 4/48* | (2018.01) |
| *G16H 40/20* | (2018.01) |

(52) U.S. Cl.
CPC ............ *B60R 16/023* (2013.01); *G16H 10/60* (2018.01); *H04L 67/12* (2013.01); *H04W 4/029* (2018.02); *H04W 4/48* (2018.02); *A61B 2560/0456* (2013.01); *G16H 40/20* (2018.01)

(58) Field of Classification Search
CPC .......... A61B 5/6893; A61B 2560/0456; B60R 16/023; H04L 67/12
See application file for complete search history.

(56) References Cited

U.S. PATENT DOCUMENTS

| | | | | |
|---|---|---|---|---|
| 6,221,012 | B1* | 4/2001 | Maschke | A61B 5/002 600/509 |
| 6,398,727 | B1* | 6/2002 | Bui | G01K 1/165 600/300 |
| 6,544,174 | B2* | 4/2003 | West | A61B 5/117 128/903 |
| 7,316,648 | B2* | 1/2008 | Kelly | G16H 40/67 128/903 |
| 9,536,254 | B1* | 1/2017 | David | G07C 5/008 |
| 10,286,143 | B2* | 5/2019 | Barnes | A61M 5/14244 |
| 2002/0072783 | A1* | 6/2002 | Goedeke | A61N 1/37223 607/60 |
| 2004/0004460 | A1* | 1/2004 | Fitch | H02J 50/70 320/108 |
| 2006/0094936 | A1* | 5/2006 | Russ | G16H 40/67 600/300 |
| 2011/0047298 | A1* | 2/2011 | Eaton | G06F 1/1632 710/304 |
| 2011/0086678 | A1* | 4/2011 | Suzuki | H04M 1/6091 455/66.1 |
| 2012/0191476 | A1* | 7/2012 | Reid | G16H 10/65 705/3 |
| 2013/0137476 | A1* | 5/2013 | Kawaguchi | H04W 4/08 455/519 |
| 2013/0179188 | A1 | 7/2013 | Hyde | |
| 2013/0317753 | A1 | 11/2013 | Kamen et al. | |
| 2014/0379369 | A1 | 12/2014 | Kokovidis et al. | |
| 2015/0025917 | A1* | 1/2015 | Stempora | G02B 27/0093 705/4 |
| 2015/0172450 | A1* | 6/2015 | Singhal | H04M 1/72463 455/419 |
| 2015/0304324 | A1* | 10/2015 | Kirsch | H04W 12/06 726/5 |
| 2015/0348338 | A1* | 12/2015 | Cho | H04L 67/12 701/32.8 |
| 2016/0075249 | A1* | 3/2016 | Grabar | B60L 53/65 320/108 |
| 2016/0188829 | A1 | 6/2016 | Southerland | |
| 2017/0041737 | A1* | 2/2017 | Fischer | H04W 4/027 |
| 2017/0104865 | A1* | 4/2017 | Skelton | H04M 1/6075 |
| 2017/0197585 | A1* | 7/2017 | Izraeli | H04W 4/80 |
| 2017/0327084 | A1* | 11/2017 | Park | B60R 16/037 |
| 2018/0006819 | A1* | 1/2018 | Watanabe | H04L 63/0428 |
| 2018/0062996 | A1* | 3/2018 | Lei | H04W 4/40 |
| 2018/0098366 | A1* | 4/2018 | Cohn | H04B 5/79 |
| 2018/0248782 | A1* | 8/2018 | Scales | H04L 43/50 |
| 2018/0276974 | A1* | 9/2018 | Talty | H04L 67/306 |
| 2018/0308570 | A1 | 10/2018 | Schmehl | |
| 2020/0020428 | A1* | 1/2020 | Avery | G16H 40/67 |
| 2020/0138288 | A1* | 5/2020 | Al-Ali | A61B 5/0015 |

FOREIGN PATENT DOCUMENTS

| | | |
|---|---|---|
| KR | 20130012286 A | 2/2013 |
| KR | 20170027766 A | 3/2017 |
| TW | 200629790 A | 8/2006 |

OTHER PUBLICATIONS

Branson et al., Monitoring During Transport (Year: 2020).*
Sagar et al., Real Time Patient Monitoring System Interfacing Metro Rail and Ambulance (Year: 2019).*
Chiarugi et al., Continuous ECG monitoring in the management of pre-hospital health emergencies (Year: 2003).*

* cited by examiner

PATIENT MONITORING

CROSS-REFERENCE TO PRIOR APPLICATIONS

This application is the U.S. National Phase application under 35 U.S.C. § 371 of International Application No. PCT/GB2018/051798, filed on Jun. 27, 2018, which claims the benefit of European Patent Application No. 1710360.7, filed on Jun. 28, 2017. These applications are hereby incorporated by reference herein.

TECHNICAL FIELD

The present invention relates to apparatus for medically monitoring patients.

BACKGROUND

Apparatus for medically monitoring patients, for example in the field, outside of an institutional medical establishment, are known. For example, Remote Diagnostic Technologies Ltd manufactures and sells such an apparatus, called the Tempus Pro™. Such apparatus generally may be used to monitor a patient and collect vital sign data using one or more medical sensors that are coupled to the apparatus. A benefit of such an apparatus is that it can be deployed remotely to the scene of an accident, for example. Ambulance vehicles may have one or more of these apparatus on board to allow paramedics to provide aid to patients. An example apparatus may allow a patient's blood pressure, temperature, and heart-rate to be monitored. Furthermore, a known apparatus may have the ability to record a patient's electrocardiogram (ECG).

Medical data gathered by the apparatus can be transmitted to other medical apparatus and/or to a remote server for storage and/or further processing. For example, a telemedicine application may access the medical data stored on the remote server. This data can provide hospital personnel with patient medical data before the patient arrives at the hospital.

SUMMARY

According to a first aspect of the present invention, there is provided an apparatus for medically monitoring a patient. The apparatus comprises at least one input to receive medical data relating to or received from a patient being monitored; memory to store the received medical data and a received vehicle identifier, which is associated with a vehicle; a communications module; and a processor. The processor is configured to generate patient data, associated with the patient being monitored, comprising the medical data and the vehicle identifier; and control the communications module to transmit the patient data to a remote server.

Such an apparatus allows medical data to be associated with a particular vehicle identifier to provide richer response capabilities by augmenting data streams with the vehicle identifier. For example, a telemedicine application may use the vehicle identifier to determine the location of the vehicle/apparatus, and therefore the patient. This can be used by personnel, such as hospital staff, to prepare for the arrival of the patient.

In some examples, the processor may be configured in a first mode to control the communications module to receive the vehicle identifier from a vehicle mounted communications device. For example, the apparatus and the vehicle mounted communications device may be communicatively coupled to allow data to be transmitted between the apparatus and the vehicle mounted communications device. The vehicle mounted communications device may be located in a vehicle for example. A vehicle mounted communications device provides a simple and effective way of providing the apparatus with the vehicle identifier.

In some examples, the processor is configured in a second mode to control the communications module to transmit the stored vehicle identifier to the vehicle-mounted communications device. In this way, the vehicle-mounted communications device can be provided with the vehicle identifier which can later be transmitted to one or more devices, such as the apparatus. Using the apparatus to provide the vehicle-mounted communications device with a vehicle identifier is a user-friendly, secure method of distributing vehicle identifiers to many different vehicle-mounted communications devices.

In some examples, the processor is configured to operate the apparatus in the second mode upon detection that the vehicle-mounted communications device is not configured with the vehicle identifier. This provides an efficient way for the user of the apparatus to determine that the vehicle-mounted communications device is not currently associated with a vehicle identifier. This may occur automatically, for example the first time that the vehicle-mounted communications device and the apparatus are communicatively coupled. In some examples this occurs without knowledge of the user.

In another example, the processor is configured to operate the apparatus in the second mode upon detection of an input from a user. By manually allowing a user to switch between the operating modes, the user is provided with a greater flexibility as to when the vehicle-mounted communications device is provided with a vehicle identifier.

In some examples, the processor is configured to arrange the patient data into one or more data packets and control the communications module to transmit the data packets to the remote server.

In some examples the processor is configured to control the communication module to receive a second vehicle identifier, which is associated with a second vehicle; and store the second vehicle identifier in the memory. This can provide a method of tracking the location of the apparatus over time as it moves from one vehicle to the next.

In some examples, the processor is configured to identify in memory which vehicle identifier is a current vehicle identifier. This can allow personnel to identify the current vehicle with which the apparatus is associated, and in some examples track the previous vehicles with which the apparatus was previously associated.

In some examples, the processor is configured to associate newly-received medical data with the current vehicle identifier. In this way, medical data can be correctly associated with the correctly vehicle identifier, even if the apparatus is moved to a new vehicle before being able to fully transmit all of the "old" data (i.e. medical data recorded earlier). Medical data recorded prior to receipt of the current vehicle identifier may be associated with the previous vehicle identifier. Associating the medical data with the vehicle identifier may include arranging the medical data into one or more data packets, and associating the one or more data packets with the corresponding vehicle identifier.

As well as storing the medical data and a vehicle identifier, the memory of the apparatus may also store one or more patient identifiers. In some examples, the memory may also store an apparatus identifier. The one or more patient identifiers may be associated with medical data from the respective patients. In one example, the processor is configured to generate patient data comprising the medical data, the vehicle identifier and a patient identifier; arrange the patient data into one or more data packets; and control the communications module to transmit the data packets to the remote server. Transmitting both the vehicle identifier and the patient identifier provides a greater wealth of information. For example, the remote server may be able to determine which patient is in which particular vehicle, and may further relay this information to a medical facility, along with medical data and/or location data.

In some examples, the communications module comprises a wireless telecommunications device to transmit the patient data to the remote server via a telecommunications network. The use of such a telecommunications network provides a wide network coverage, increasing the likelihood of good connectivity to the remote server.

In some examples, the communications module comprises a wired interface to receive the vehicle identifier from the vehicle-mounted communications device. In some examples, using a wired connection means that power can be provided at the same time.

In some examples, the vehicle-mounted communications device, is, or comprises a docking station and the apparatus is adapted to be mounted in the docking station. The apparatus may therefore be communicatively coupled with the docking station by placing or mounting the apparatus within the dock, and a communications path may be established as a result. A docking station provides a simple and effective way of establishing a data communications path with the apparatus to provide, or receive, the vehicle identifier.

According to one example, the docking station is configured to be communicatively coupled to a second docking station, and the second docking station is adapted to receive a second kind of medical apparatus. The processor is configured to: responsive to when the apparatus is docked in the docking station and to when the second kind of apparatus is docked in the second docking station, establish a wireless communications channel between the apparatus and the second kind of apparatus. To establish the wireless communications channel, the processor may be configured to initially automatically pair the apparatus with the second kind of apparatus. In this way, whenever one or both of the apparatus and second apparatus are removed from their respective docking stations, the devices are already paired, and the connected via the wireless communications channel. This removes the need for the user(s) to manually connect the two devices, using existing cumbersome connection procedures. This allows the user(s) to attend to a patient's needs quicker, thus potentially saving lives.

In one example, the processor is configured to: generate patient data comprising the medical data, the vehicle identifier and a status indicator, wherein the status indicator indicates whether the apparatus is communicatively coupled to the vehicle mounted communications device. Transmission of the status indicator may be beneficial to determine, with greater probability, whether the apparatus is indeed located in the vehicle indicated by the vehicle identifier. For example, medical personnel can be certain that the apparatus is located in a vehicle if the status indicator indicates that the apparatus is currently communicatively coupled to the vehicle mounted communications device of that vehicle. If the status indicator indicates the apparatus is not currently communicatively coupled to the vehicle mounted communications device, but nevertheless still transmits a vehicle identifier associated with a vehicle, the location of the apparatus may be taken to be less accurate.

According to a second aspect of the present invention, there is provided a system for medically monitoring a patient, the system comprising an apparatus and a vehicle-mounted communications device. The vehicle-mounted communications device comprises memory to store a vehicle identifier which associated with a vehicle and a communications module to transmit the vehicle identifier to the apparatus. The apparatus comprises at least one input to receive medical data relating to or received from a patient; memory to store the received medical data and the vehicle identifier; a communications module; and a processor. The processor is configured to: control the communications module of the apparatus to receive the vehicle identifier from the vehicle-mounted communications device; generate patient data, associated with the patient being monitored, comprising the medical data and the vehicle identifier; and control the communication module of the apparatus to transmit the patient data to a remote server.

In some examples, the system may further comprise the remote server, wherein the remote server is configured to receive the patient data from the apparatus. As briefly mentioned above, the remote server can use the vehicle identifier to determine the location of the vehicle and therefore the patient and apparatus. This allows the medical data to be associated with a location, so that personnel can determine where the patient is at any one time by obtaining location information associated with the vehicle using the vehicle identifier. Therefore, in some examples, the remote server is configured to obtain, using the vehicle identifier, location information associated with the vehicle.

In some examples, data, associated with the location information and the received medical data, is sent by the remote server, to a medical facility. This allows personnel at the medical facility to determine the location of the patient.

According to some examples, the vehicle-mounted communications device comprises a docking station and the apparatus is adapted to be mounted in the docking station.

In some examples, the system further comprises a second kind of apparatus; and a second docking station which is adapted to receive the second kind of medical apparatus, the second docking station being configured to be communicatively coupled to the docking station. The processor of the apparatus may be configured to: responsive to when the apparatus is docked in the docking station and to when the second kind of apparatus is docked in the second docking station, establish a wireless communications channel between the apparatus and the second kind of apparatus.

According to a third aspect of the present invention, there is provided a method. The method comprises receiving, by an apparatus, a vehicle identifier which is associated with a vehicle; receiving, by the apparatus, medical data relating to or received from a patient; generating patient data, associated with the patient, comprising the medical data and the vehicle identifier; and transmitting, by the apparatus, the patient data to a remote server.

According to a fourth aspect of the present invention there is provided a non-transitory computer readable storage medium comprising a set of computer-readable instructions stored thereon, which, when executed by a processor, cause the processor to, implement method according to the third aspect, or any method described herein.

As mentioned above, data may be transmitted between the apparatus and a second kind of apparatus, for example wirelessly, via Bluetooth. A connection therefore needs to be established and maintained. Currently, the connection procedure used to establish the connection between two devices is cumbersome and lengthy. The process often needs to be done quickly and efficiently, which is especially important in times of emergency. To connect two devices, they may first need to be "paired". Once paired, a wireless communications channel can be established between the apparatus and the second apparatus to allow the transfer of data.

To speed up this pairing and connection procedure, devices can be configured to use an "auto-pair" procedure. This procedure can be initiated by coupling two devices together via a wired connection. As one device detects the presence of the other device, the devices can be automatically paired and establish a wireless communications channel. This can occur without the need for user intervention, or with reduced user intervention as compared to standard procedures.

According to a fifth aspect of the present invention there is provided a first patient monitor apparatus for medically monitoring a patient. The first patient monitor apparatus comprises a communications module comprising first and second communication interfaces; and a processor. The processor is configured to: responsive to when the first patient monitor apparatus is communicatively coupled to a second patient monitor apparatus via the first communication interface, pair the first patient monitor apparatus with the second patient monitor apparatus. For example, the first patient monitor apparatus (for example the processor or another module) may determine that the first patient monitor apparatus is communicatively coupled to a second patient monitor apparatus. Pairing may occur if the first patient monitor apparatus and the second patient monitor apparatus have not previously been paired and occur prior to establishing the wireless communications channel. In some examples, pairing is automatic.

In some examples the first patient monitor apparatus is adapted to be received in a first docking station, and the first docking station is configured to be communicatively coupled to a second docking station, which is adapted to receive the second patient monitor apparatus. The processor of the first patient monitor apparatus may be configured to: pair the first patient monitor apparatus with the second patient monitor apparatus in response to detecting when the first patient monitor apparatus is docked in the first docking station and the second patient monitor apparatus is docked in the second docking station.

In some examples the processor is further configured to establish a wireless communications channel between the first patient monitor apparatus and the second patient monitor apparatus via the second communication interface.

In some examples, to pair the first patient monitor apparatus with the second patient monitor apparatus, the processor is configured to: initiate a pairing procedure using the second communication interface; and transmit an instruction to the second patient monitor apparatus via the first communication interface to initiate a pairing procedure at the second patient monitor apparatus. Accordingly, the first patient monitor apparatus can control and configure the pairing procedure between the first patient monitor apparatus and the second patient monitor apparatus.

According to a sixth aspect of the present invention there is provided a system for medically monitoring a patient. The system comprises a first patient monitor apparatus and a second patient monitor apparatus. The first patient monitor apparatus comprises: a communications module comprising first and second communication interfaces; and a processor. The processor is configured to: responsive to when the first patient monitor apparatus is communicatively coupled to the second patient monitor apparatus via the first communication interface, pair the first patient monitor apparatus with the second patient monitor apparatus.

In some examples, the system further comprises a first docking station adapted to receive the first patient monitor apparatus; and a second docking station, adapted to receive the second patient monitor apparatus. The first docking station is configured to be communicatively coupled to the second docking station. The processor is configured to pair the first patient monitor apparatus with the second patient monitor apparatus in response to detecting when the first patient monitor apparatus is docked in the first docking station and the second patient monitor apparatus is docked in the second docking station.

In some examples, the processor is further configured to establish a wireless communications channel between the first patient monitor apparatus and the second patient monitor apparatus via the second communication interface.

In some examples, to pair the first patient monitor apparatus with the second patient monitor apparatus, the processor is configured to initiate a pairing procedure using the second communication interface; and transmit an instruction to the second patient monitor apparatus via the first communication interface to initiate a pairing procedure at the second patient monitor apparatus.

According to a seventh aspect of the present invention there is provided a method comprising: determining that a first patient monitor apparatus is communicatively coupled to a second patient monitor apparatus via a first communication interface; and pairing the first patient monitor apparatus with the second patient monitor apparatus via a second communication interface.

In some examples, the method further comprises establishing a wireless communications channel between the first patient monitor apparatus and the second patient monitor apparatus via the second communication interface.

In some examples, determining that the first patient monitor apparatus is communicatively coupled to a second patient monitor apparatus via a first communication interface comprises receiving an indication via the first communication interface. In some examples the indication is received in response to a query sent from the first patient monitor apparatus to the second patient monitor apparatus via the first communication interface.

In some examples pairing the first patient monitor apparatus with the second patient monitor apparatus via the second communication interface, comprises: initiating a pairing procedure using the second communication interface; and transmitting an instruction to the second patient monitor apparatus via the first communication interface to initiate a pairing procedure at the second patient monitor apparatus.

Further features and advantages of the invention will become apparent from the following description of preferred embodiments of the invention, given by way of example only, which is made with reference to the accompanying drawings.

DETAILED DESCRIPTION

Figure 1:
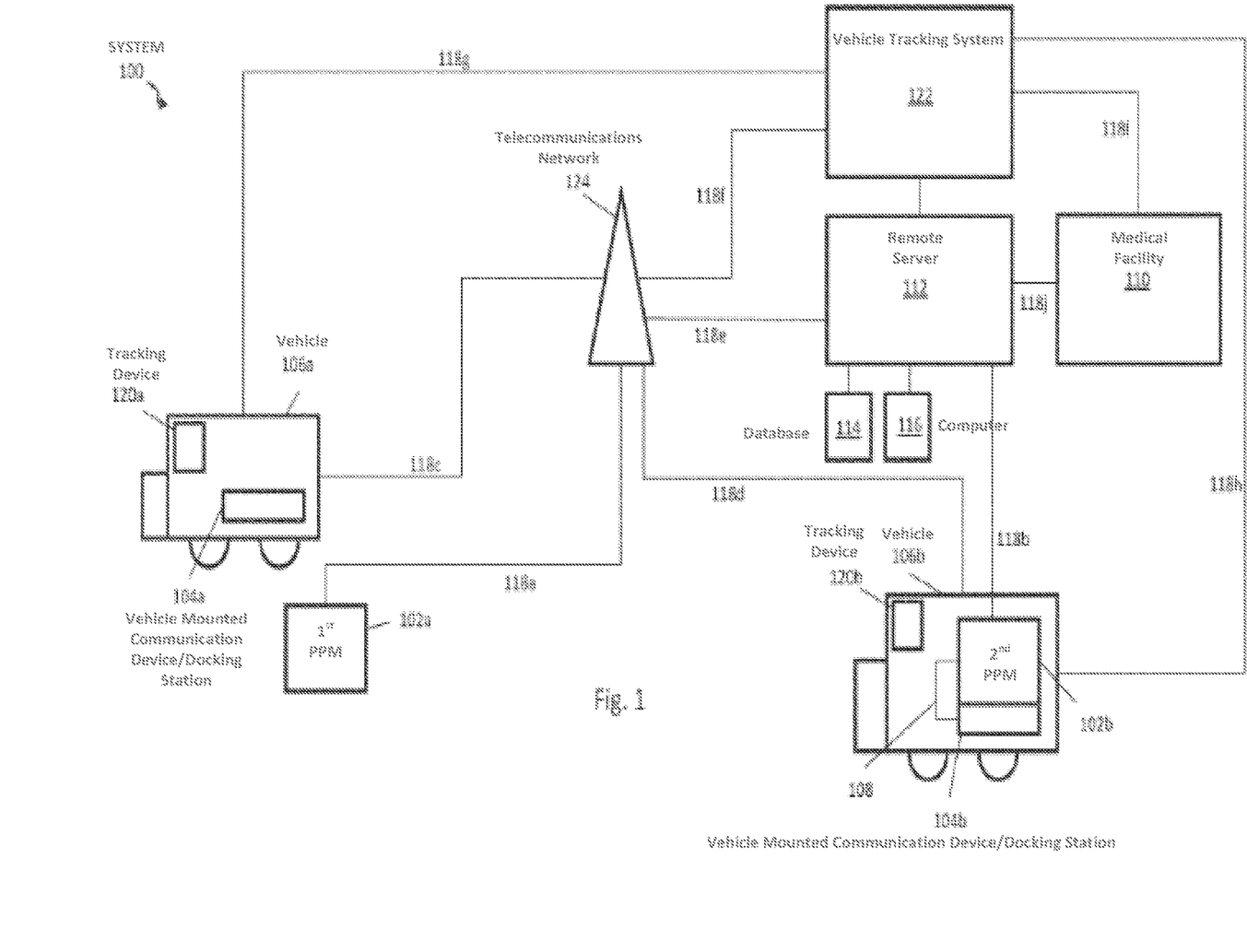
FIG. 1 is a block diagram of an example system in which an apparatus for medically monitoring patients may be used.

FIG. 1 depicts an example system 100 in which first and second apparatus, 102a, 102b, for medically monitoring patients, may be used. Each apparatus 102a and 102b will be referred to hereafter as a portable patient monitor (PPM). The first PPM 102a may be associated with a vehicle-mounted communications device 104a on a first vehicle 106a, and the second PPM 102b may be associated with a vehicle-mounted communications device 104b on a second vehicle 106b. In this example, the vehicle-mounted communications devices 104a, 104b are depicted as being inside vehicles 106a, 106b, respectively, although, in other examples, the vehicle-mounted communications devices 104a, 104b may be affixed to the exterior of the respective vehicles 106a, 106b.

In the system of FIG. 1, unless otherwise stated, the PPM 102a is identical to the PPM 102b. For convenience, the following discussion will refer generally to the PPM 102a, vehicle 106a, vehicle-mounted communications devices 104a and tracking device 120a, however any statement equally applies to the PPM 102b, vehicle 106b, vehicle-mounted communications device 104b and tracking device 120b unless otherwise stated.

The PPM 102a can be used to medically monitor patients. For example, the PPM 102a can be used to measure a patient's blood pressure, temperature and heart-rate. Furthermore, the PPM 102a may have the ability to record a patient's ECG. In some examples the PPM 102a may include or be associated with equipment to function as a defibrillator. It will be appreciated that the PPM 102a may perform any number of medical monitoring functions.

Medical personnel, such as a paramedic, may use the PPM 102a during an emergency. For example, one can imagine the scenario where one or more patients have been involved in a car accident and one or more paramedics are called upon to provide assistance. A paramedic may arrive at the scene of the accident in a vehicle 106a, such as an ambulance, which is equipped with the PPM 102a. Using the PPM 102a, the paramedic is able to monitor and/or treat each patient at the scene of the accident, away from the ambulance, as well as doing so while travelling to a medical facility 110, while inside the vehicle 106a. Example medical facilities 110 may include a hospital or doctor's surgery. Other example vehicles may include military vehicles, boats and aircraft.

The PPM 102a may comprise at least one input, such as a medical sensor, to receive medical data from the patient. The PPM 102a may then relay patient data to a remote server 112, which stores the data in a database 114. The data may be accessed at the server 112, or remotely on another computer such as a PC or handheld device, using a software application such as a telemedicine application. Data may be exported to other systems, such as a system within the medical facility 110 or other systems (not shown) that have the requisite permissions to access the data. Medical personnel, such as the operator of the computer 116, or personnel within the medical facility 110, can thereby access data obtained from the PPM 102a.

The PPM 102a may comprise local and wide area network communications capabilities as part of a communications module. For example, the PPM 102a may support local communications via one or more of Wi-Fi, ZigBee, NFC and Bluetooth communications protocols in addition to wide area communications via one or more of point-to-point radio, cellular (e.g. one or more of 2G, 3G, 4G, 5G, and beyond etc.) and even satellite communications capabilities. Thereby, patient data can be transmitted wirelessly to the remote server 112. The data may be sent using a known Internet protocol over one or more of the aforementioned local or wide communications channels. Illustrative data connections from the PPMs 102a, 102b to a telecommunications network 124 are depicted by respective communication paths 118a, 118b.

The vehicles 106a, 106b, may contain on-board tracking units 120a, 120b and may also have cellular or other telecommunications capabilities, independently of the PPMs 102a, 102b, which can communicate wirelessly via the telecommunications network 124. Data connections from the vehicles 106a, 106b to the telecommunications network 124 are depicted by communication paths 118c, 118d. A data connection from the telecommunications network 124 to the remote server 112 is depicted by communication path 118e. All data connections 118 may be one-way or two-way as need dictates.

The PPM 102a may be communicatively coupleable to a respective vehicle-mounted communications device 104a. A vehicle-mounted communications device 104a may also act as a power source for the PPM 102a. For example, the PPM 102a may be electrically coupleable, via an appropriate electrical coupling, to the vehicle-mounted communications device 104a to power the PPM 102a and re-charge a rechargeable battery within the PPM 102a. Therefore, the PPM 102a may be coupled to the vehicle-mounted communications devices 104a to charge its battery, and the PPM 102a may still function while they are so coupled.

In the example of FIG. 1, the vehicle-mounted communications device 104a comprises a docking station 104a and the PPM 102a is adapted to be mounted in the docking station. Hence, the PPM 102a may be docked with the docking station 104a. Similarly, the PPM 102b may be docked with the docking station 104b. Either or both of communications coupling and electrical coupling between the PPM 102a and its docking station 104a may be via one or more appropriate physical connections that are made when the PPM 102a is docked in the docking station 104a. In the scenario of FIG. 1, the PPM 102a is depicted as being undocked from the docking station 104a and PPM 102b is depicted as being docked with the docking station 104b and having a communication path 108 therebetween. Communications coupling between a PPM 102a and a vehicle-mounted communications device 104a may be via physical or wireless channels. Therefore, communication path 108 may be illustrative of a cable or other connector (e.g. an upstanding male connector in the docking station 104b which marries with a female connector in the PPM 102b). Alternatively, communications path 108 may be a Bluetooth or Wi-Fi channel, for example.

According to examples herein, a PPM 102a may be docked in a docking station 104a of a vehicle 106a when not in use to ensure that the PPM 102a is fully re-charged when it is needed.

In the example depicted in FIG. 1, where the vehicle-mounted communications device 104a comprises a docking station, communicative coupling and transfer of data between the PPM 102a and the docking station 104a can occur when the PPM 102a is docked in the docking station 104a.

A vehicle-mounted communications device 104a may be located within a particular vehicle 106a and rarely, if ever, move to a different vehicle. Conversely, a PPM 102a may often be moved from one vehicle 106a to another. For example, a paramedic may use a particular PPM 102a and may take that PPM 102a to a different vehicle over the course of a working day. This may occur, for example, if a PPM 102a that is monitoring a patient in one ambulance 106a accompanies the patient into a hospital 110 and is then redeployed to another ambulance 106b when it is no longer needed. For reasons that will become apparent, it is important to know where each PPM 102a is (i.e. in which vehicle each PPM 102a resides). Similarly, it may be helpful to determine where a patient is at any given time.

As has already been mentioned, existing vehicles 106a, 106b, such as ambulances, may have their own tracking devices 120a, 120b on-board, which can be used to determine the location of a respective vehicle 106a, 106b. Such tracking systems are known and may comprise a combination of a GPS receiver and one or more communications devices so that GPS location information can be detected and communicated to a remote system. For example, by detecting periodic signals from the tracking devices 120a, 120b, a vehicle tracking system 122 can keep track of the location of multiple vehicles 106a, 106b in near real-time. A database (not shown) within the vehicle tracking system 122 may store the current or most recent location of the vehicles 106a, 106b. The vehicle tracking system 122 may be able to use the location information to ascribe estimated times of arrival of a vehicle 106a to a patient's location or to a medical facility 110 using known route calculation methods and systems.

Location information associated with each vehicle may be associated with a vehicle identifier that uniquely identifies the vehicle 106a. Hence the tracking system 122 may store a vehicle identifier with respective location information for each vehicle. The vehicle identifier may also be stored within the tracking device 120a and/or be sent from the tracking device 120a to the vehicle tracking system 122 with respective location information.

Data from the tracking devices 120a, 120b may be sent to the vehicle tracking system 122 via the telecommunications network 124, for example via the illustrated communication paths 118c, 118d and 118f. Alternatively, the data may be sent via communication paths 118g, 118h (which may include radio networks, satellite networks, or proprietary networks, for example).

Accordingly, an operator of the vehicle tracking system 122 is able to determine the location of the vehicle 106a or the vehicle 106b. Such an operator, who may be part of a vehicle or fleet management organisation, for example an ambulance dispatch unit, may on demand be able to notify a medical facility 110 of the location of the particular vehicle 106a (via communication path 118i). However, the operator would typically not know the identity of a patient being transported or their medical condition. Equally, while the medical facility 110 may separately have access to the medical data, received from a PPM and accessed from the remote server 112 (via communication path 118j), it is unlikely to know an identity of a respective ambulance or the location thereof.

Examples herein comprise a PPM 102a which is adapted and arranged to augment medical data with information regarding the identity of the vehicle 106a with which the PPM 102a is associated. This can be achieved by arranging the PPM 102a, to transmit a respective vehicle identifier to the remote server 112 with, or separate from, the medical data that has been collected and generated by the PPM 102a. For example, the PPM 102a may generate patient data, associated with the patient being monitored, comprising the medical data and the vehicle identifier. Accordingly, the remote server 112 can be arranged to use received patient data to determine the location of the vehicle 106a and its in-bound patient. This is achieved by querying the vehicle tracking system 122 using the vehicle identifier. The vehicle tracking system 122 may be arranged to provide to the remote server 112 the location of the vehicle 106a and/or the expected time of arrival of the vehicle 106a at the medical facility 110. Hence, an operator of computer 116 or within the medical facility 110 can associate a patient's medical data with a particular vehicle 106a, a respective location of the vehicle 106a and patient, and even an expected time of arrival of the vehicle 106a and its patient. Alternatively, or additionally, an operator of computer 116 or within the medical facility 110 can use the respective location of the vehicle 106a and patient to determine/calculate an expected time of arrival of the vehicle 106a and its patient at the medical facility 110. The usefulness of a telemedicine application therefore vastly increases because the medical facility 110 can more accurately prepare for the patient's arrival ahead of time. Moreover, the locations of the PPM 102a can be tracked, by reference to the vehicle it resides in, which reduces the likelihood of the PPM 102a being lost or misplaced. Tracking the location of the PPM 102a can also mean that the PPM 102a can be quickly and efficiently located so that an engineer can perform software updates, run status reports or perform repairs for example; this may be particularly useful if the PPM 102a does not have location tracking capabilities of its own.

Some PPMs 102a, 102b may have location determining capabilities of their own, for example they may be equipped with GPS receivers. However, it may not always be practical to use them. For example, such GPS receivers use additional battery power, which may not be desirable, or the GPS receivers may not work reliably in areas with poor signal, for example inside a vehicle 106a. By having the PPM 102a transmit a vehicle identifier to the remote server 112 (as part of the patient data), the respective location can be determined from the vehicle tracking system 122 instead. This means that the GPS functionality of the PPM 102a need not be used (if it has such functionality) therefore extending the battery and operating lifetime of the PPM 102a before it needs recharging. This extends the operating time of the potentially lifesaving PPM 102a. Furthermore, using the vehicle identifier may also be beneficial if the GPS functionality of the apparatus is less accurate, or includes less information than is gathered by the vehicle tracking system 122.

As mentioned above, a tracking device 120a may store or transmit a vehicle identifier to the vehicle tracking system 122. Additionally, or alternatively, the vehicle tracking system 122 may store a vehicle identifier that is associated with location information gathered by the vehicle tracking system 122. In one example, the vehicle identifier used by the vehicle tracking system 122 is the same as that transmitted by the PPM 102a to the remote server 112. However, this need not necessarily be the case. The remote server 112 (or database 114) or the vehicle tracking system 122 may instead store an association between two different vehicle identifiers; one associated with the tracking device 120*a* and one associated with the PPM 102*a*. In other words, using the vehicle identifier transmitted by the PPM 102*a* the correct location information can be obtained. The remote server 112 may receive the vehicle identifier from the PPM 102*a* and query a database to find an association with a different vehicle identifier used within the vehicle tracking system 122. Accordingly, a mapping between vehicle identifiers is performed and the correct location information may thereby be obtained.

Initially, the PPM 102*a* needs to obtain, or be associated, with a vehicle identifier in order for it to be transmitted back to the remote server 112.

In one example, the PPM 102*a* receives the vehicle identifier from the vehicle mounted communications device 104*a*. For example, the vehicle mounted communications device 104*a* is associated with a vehicle identifier and communicatively coupling the PPM 102*a* with the vehicle mounted communications device 104*a* allows the PPM 102*a* to receive the vehicle identifier. When the PPM 102*a* receives the vehicle identifier from the vehicle mounted communications device 104*a*, the PPM 102*a* may be configured in a first mode to control a communications module to receive the vehicle identifier from the vehicle mounted communications device 104*a*.

In another example, the PPM 102*a* receives the vehicle identifier from an external source.

In another example, a user of the PPM 102*a* programs the PPM 102*a* with a vehicle identifier (or it is automatically generated by the PPM 102*a*). The vehicle identifier used by the vehicle tracking system 122 (and tracking device 120*a*) may be printed on a label in the vehicle 106*a* or on the vehicle tracking device 120*a* for example, and the user may enter this into the PPM 102*a* via a keyboard or scan it into the PPM using a QR code.

Regardless of how the PPM 102*a* receives/obtains a vehicle identifier, it is beneficial to store the vehicle identifier in the vehicle-mounted communications device 104*a* itself. Doing so associates the vehicle-mounted communications device 104*a* with the vehicle identifier of a particular vehicle 106*a* within which the vehicle-mounted communications device 104*a* is located. Hence, initially, the vehicle mounted communications device 104*a* needs to obtain a vehicle identifier before it can transmit this to the PPM 102*a*.

According to one example, the PPM 102*a* can be initially used to transfer a vehicle identifier to the vehicle mounted communications device 104*a*. For example, the PPM 102*a* may be configured in a second mode of operation to transfer a stored vehicle identifier to the vehicle-mounted communications device 104*a*. This may be arranged to occur, for example, the first time a docking station of the vehicle-mounted communications device 104*a* is docked with a PPM.

One method of using the PPM 102*a* to associate a vehicle identifier with the vehicle-mounted communications device 104*a* will be explained. However, it should be appreciated that many other methods may be used. Initially, the PPM 102*a* is caused to be communicatively coupled with the vehicle-mounted communications device 104*a*. For example, if the vehicle-mounted communications device 104*a* comprises a docking station, the PPM 102*a* is docked and connected to the docking station. When the PPM 102*a* and vehicle-mounted communications device 104*a* are communicatively coupled, the vehicle identifier can be transferred from the PPM 102*a* to the vehicle-mounted communications device 104*a*. The user may manually enter the vehicle identifier at this time, or it may already be stored within memory of the PPM 102*a* (as described above). The PPM 102*a* may be operating in a second mode at this time, where, in the second mode, the vehicle-mounted communications device 104*a* can be associated with a vehicle identifier, by transmitting the vehicle identifier to the vehicle mounted communications device 104*a*. The PPM 102*a* may detect that the vehicle-mounted communications device 104*a* is not configured with a vehicle identifier and automatically enter the second mode and transfer the vehicle identifier as a result. Alternatively, the user may manually cause the PPM 102*a* to enter the second mode and transfer the vehicle identifier to the vehicle-mounted communications device 104*a*. Manually entering the first, second, or any mode may include detecting that a user has pressed a button, or provided an indication via a user interface.

As can be seen, the PPM 102*a* can be used to associate the vehicle-mounted communications device 104*a* with a vehicle identifier. As mentioned, when the PPM 102*a* receives the vehicle identifier from the vehicle-mounted communications device 104*a*, the PPM 102*a* may be said to be operating in a first mode. Entering the first mode may occur automatically, for instance as soon as the PPM 102*a* is docked on the vehicle-mounted communications device 104*a* (or in any other way establishes physical or wireless communicative coupling with the vehicle-mounted communications device 104*a*), or the user may manually enter the first mode in which the PPM 102*a* can receive the vehicle identifier from the vehicle-mounted communications device 104*a*. The PPM 102*a* may detect that the vehicle-mounted communications device 104*a* is configured with a vehicle identifier and automatically request the vehicle identifier. Once the PPM 102*a* has received the vehicle identifier, it can transmit sensed medical data to the remote server 112 along with the vehicle identifier.

In one example, the sensed medical data and vehicle identifier are transmitted to the remote server 112 together. For example, the PPM 102*a* may first generate patient data, associated with the patient being monitored, where the patient data comprises the medical data and the vehicle identifier. This patient data may then be transmitted to the remote server 112.

In another example, the sensed medical data and vehicle identifier are sent separately and are associated at a later time.

In another example, the PPM 102*a* may also be configured to transmit, periodically, a status indicator to the remote server. This status indicator may be sent with the vehicle identifier, for example as part of the patient data. The status indicator may indicate whether the PPM 102*a* is communicatively coupled to the vehicle mounted communications device 104*a*. This may be sent as a flag, such as a predefined bit or bit sequence in a Data stream, for example. In an example, where the vehicle mounted communications device 104*a* comprises a docking station, the PPM 102*a* may be configured to transmit a status indicator indicating that the PPM 102*a* is docked only when the PPM 102*a* is mounted on or within the docking station. If the PPM 102*a* is removed from the docking station, the status indicator may indicate that the PPM 102*a* is undocked.

Transmission of the status indicator may be beneficial to determine, with greater certainty, whether the PPM 102*a* is indeed associated with the vehicle indicated by the vehicle identifier. For example, an operator of the computer 116, or personnel within the medical facility 110, can be certain that the PPM 102*a* is located in the vehicle 106*a* if the status indicator indicates that the PPM 102*a* is currently communicatively coupled to (or docked on) the vehicle mounted communications device 104a of that vehicle 106a. If the status indicator indicates the PPM 102a is not currently communicatively coupled to (or docked on) the vehicle mounted communications device 104a, but nevertheless still transmits a vehicle identifier associated with vehicle 106a, the location of the PPM 102a and/or its correct association with the respective vehicle may be taken to be less certain. For example, if the PPM 102a is transferred to a different vehicle 106b, such as another ambulance or even a helicopter, it may continue to transmit the existing vehicle identifier until such time as a new vehicle identifier is uploaded. Under such situations, at least initially, the vehicle identifier, and by inference the location of the vehicle, could be misleading. In some examples, when the status indicator indicates that the PPM 102a is not currently communicatively coupled to the vehicle mounted communications device 104a, the GPS functionality of the PPM 102a may be invoked to determine a more certain location of the PPM 102a.

According to one example, the patient data including the vehicle identifier is transmitted to the remote server 112 only when the PPM 102a has determined that it is coupled to the vehicle-mounted communications device 104a (i.e. when the status indicator indicates that the PPM 102a is communicatively coupled to the vehicle mounted communications device 104a). Medical data (without the vehicle identifier) may be transmitted when the PPM 102a is not coupled to the vehicle-mounted communications device 104a. In other examples the vehicle identifier can be transmitted to the remote server 112 in absence of medical data, regardless of whether the PPM 102a has determined that it is coupled to the vehicle-mounted communications device 104a.

Sending or transmitting data may include arranging the patient data into one or more data packets. The vehicle identifier (and/or status indicator) may be included in each of the data packets. Alternatively, the vehicle identifier (and/or status indicator) may be included in only one, or a portion of the data packets. A unique patient identifier, which is assigned to each patent, may similarly be included in the data packets. Similarly, a unique PPM identifier may be included in some or all of the data packets. Hence patient data may also include a patient identifier and/or PPM identifier.

As briefly mentioned, a PPM 102a may be moved from one vehicle to another. It is therefore necessary to associate the PPM 102a with a new vehicle identifier for that particular vehicle. This ensures that newly-received medical data is associated with the correct vehicle identifier. Associating the PPM 102a with a new, second vehicle identifier is performed substantially in the same way in which the PPM 102a is associated with its first vehicle identifier. For instance, the PPM 102a may be communicatively coupled with a new, second (or subsequent) vehicle-mounted communications device.

In the following example, it is assumed that PPM 102a is associated with the vehicle-mounted communications device 104a initially, and the PPM 102a has a vehicle identifier (associated with vehicle 106a) stored in its memory. The PPM 102a is then transferred to the second vehicle 106b.

Initially, a user causes the PPM 102a, to be communicatively coupled with the second vehicle-mounted communications device 104b in the second vehicle 106b. This causes a second vehicle identifier to be received from the second vehicle-mounted communications device 106b. This second vehicle identifier is then stored in the memory of the PPM 102a.

The PPM 102a may now be un-coupled (for instance, un-docked) from the second vehicle-mounted communications device 104b. In one example, storing the second vehicle identifier in memory means that the previous vehicle identifier is overwritten. This may occur, for instance, if all patient data collected while the PPM 102a was associated with the former vehicle has been relayed to the remote server 112. Alternatively, the second vehicle identifier is stored as well as the previous vehicle identifier. In some examples the second, most recent vehicle identifier is "tagged" as the current vehicle identifier. This may be done by determining which vehicle identifier was received most recently, for example by use of a time stamp.

Any newly-received medical data collected by the PPM 102a may then be associated with this second vehicle identifier, instead of with the previous vehicle identifier. In doing so, the location of the PPM 102a can be monitored by reference the location of the second vehicle. In this way, medical data can be associated correctly with the correct vehicle identifier.

Figure 2:
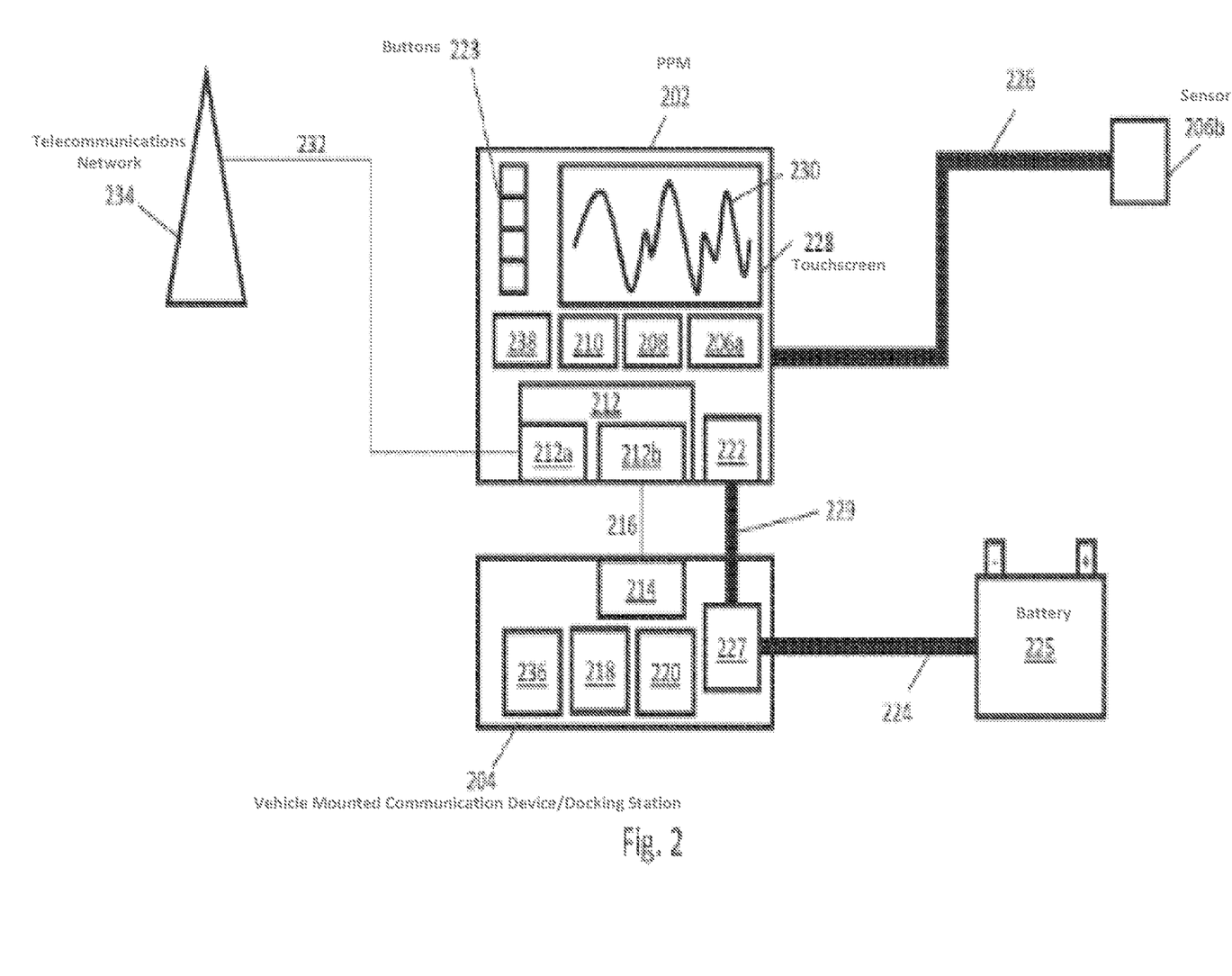
FIG. 2 is a block diagram of an example apparatus for medically monitoring patients and a vehicle mounted communications device.

In some instances, the PPM 102a may still have "old" medical/patient data stored within memory, where this old medical data was recorded at an earlier time when the PPM 102a was still associated with a first vehicle 106a, rather than with a subsequent vehicle 106b. This data may be transmitted to the remote server 112 even after the PPM 102a has been moved to the second vehicle 106b. This "old" medical data will be associated with the previous vehicle identifier, and so, regardless of when data is uploaded to the remote server 112, the data remains associated with the correct vehicle identifier. FIG. 2 depicts an example of an apparatus comprising a PPM 202 for medically monitoring patients and an apparatus comprising a vehicle mounted communications device 204. The PPM 202 is identical to PPM 102a and 102b depicted in FIG. 1. Similarly, vehicle mounted communications device 204 is identical to the vehicle mounted communications devices 104a and 104b depicted in FIG. 1.

The PPM 202 comprises at least one input to receive medical data from a patient. Medical data may be manually entered, or be received from one or more medical sensors 206a, 206b, used to sense/measure medical data from a patient. The PPM 202 further comprises memory 208 and a processor 210. The processor 210 may be configured to generate patient data, associated with the patient being monitored, where the patient data comprises the medical data and the vehicle identifier. The memory 208 may be configured to store any sensed and collected medical data and one or more vehicle identifiers. In some examples, the memory 208 can also store the patient data, one or more patient identifiers, and/or a PPM identifier, and/or a status indicator. The PPM 202 may also comprise one or more communication interfaces 212a, 212b as part of a communications module 212. The processor 210 may be configured to control the communications module 212 (and hence the one or more communication interfaces 212a, 212b). For example, communication interface 212b may be controlled to receive a vehicle identifier from the vehicle-mounted communications device 204. The same, or different communication interface 212a may be controlled to transmit the patient data to a remote server 112.

The communication interfaces 212a, 212b may be wired or wireless interfaces, such as USB, Firewire, Ethernet, WiFi, GPS, Bluetooth, satellite interfaces, telecommunications interfaces (GSM, 3G, 4G) or any other standard or proprietary interfaces. In the example of FIG. 2, the communication interface 212b is a wired interface and the communication interface 212a is a wireless interface. In other examples, both of the communication interfaces 212a, 212b may be wireless or both may be wired interfaces.

As mentioned with regard to FIG. 1, the PPM 202 can be communicatively coupled to the vehicle-mounted communications device 204. In some examples communicative coupling requires a data connection to be established between a communication interface 212b of the PPM 202 and a communication interface 214 of the vehicle-mounted communications device 204. In the example of FIG. 2, a communication path 216 is shown between the communication interface 212b of the PPM and the communication interface 214 of the vehicle-mounted communications device 204, across which (in one mode) the PPM 202 may provide the vehicle-mounted communications device 204 with a vehicle identifier and (in another mode) the PPM 202 may receive a vehicle identifier from the vehicle-mounted communications device 204.

The vehicle identifier may be stored in a memory 218 of the vehicle-mounted communications device 204. According to one example the memory 218 is non-volatile memory, such as a hard disk, Flash storage chip, or SSD. In one example, the vehicle-mounted communications device 204 comprises a USB device comprising the memory 218 and/or a USB communication interface 214. A controller 220 of the vehicle-mounted communications device 204 may control the vehicle-mounted communications device 204 and its one or more communication interfaces 214. The controller 220 may be a USB controller, a microcontroller, or a processor, for example. In one example, the vehicle-mounted communications device 204 is a dock and comprises a structure or frame, for receiving and supporting at least one PPM, and a controller, such as a USB hub controller, to which the, or each, PPM couples, via one or more physical connections (e.g. USB connections) 214, when docked. In such an example, the USB hub controller may be programmable and provide memory 218 for storing data such as vehicle identifier. In any event, the controller 220 may cause or allow the vehicle identifier to be written to memory 218, or cause or allow the vehicle identifier be transferred to a PPM via the communication interface 214. The controller 220 may be optional. As with the PPM 202, the communication interface 214 of the vehicle-mounted communications device 204 may be part of a respective communication module.

When the PPM 202 is communicatively coupled to the vehicle-mounted communications device 204, the PPM 202 may also be electrically coupled thereto, to enable a battery 222 within the PPM 202 to be charged. A power source such as a vehicle battery 225 and/or alternator of an ambulance may supply power to the vehicle-mounted communications device 204 via a power cable 224, which may in turn charge the battery 222 of the PPM 202 via an appropriate charge controller 227 and connector 229.

Alternatively, the battery 222 may be charged via wireless, inductive charging. In some examples, separate interfaces are used to charge the PPM 202, however in other examples power may be supplied via the communication interfaces 212b, 214.

The medical sensors of the PPM 202 may be integral with the PPM 202 (as is 206a), or may be external (as is 206b). External sensors 206b may be connected to the PPM 202 via a sensor cable 226. Medical data sensed by the medical sensors 206a, 206b may be stored within the memory 208. The processor 210 may also process the medical data before the patient data is transmitted to the remote server 112 (shown in FIG. 1). Any sensed medical data (which includes processed medical data) may be displayed on a display screen 228. FIG. 2 depicts a portion of medical data 230 being displayed. The display 228 may be a touchscreen, and accept input from a user for instance via interaction with displayed selection keys or an alphanumeric keyboard. Alternatively, or additionally, the PPM 202 may also comprise one or more physical buttons 223. Using the touchscreen 228 or buttons 223, a user may enter patient treatment record data and control or configure the PPM 202. For example, the user may be able to instruct the PPM 202 to transmit data to the remote server 112. The user may also be able to switch between the first and second mode, as described above.

Data may be sent from the PPM 202 to the remote server 112 via the communication interface 212a, communication path 232 and telecommunications network 234. As described, this data, or the one or more data packets into which the data is organised, may also include one or more patient identifiers and/or a PPM identifier and/or a status indicator. For example, the patient data generated by the processor may comprise the medical data, the vehicle identifier, a patient identifier and a status indicator.

The PPM 202 may also comprise a status indicator module 238. The status indicator module 238 may be embodied as hardware or software, or a combination thereof. In one example, the processor 210 comprises a status indicator module 238. The status indicator module 238 may be configured to detect or determine when the PPM 202 is communicatively coupled to the vehicle-mounted communications device 204. Based on this determination, a status indicator can be updated to reflect whether the PPM 202 is coupled or not coupled to the vehicle-mounted communications device 204. In some examples, the vehicle-mounted communications device 204 may also comprise a similar status indicator module 236 that is configured to detect or determine when the PPM 202 is communicatively coupled to the vehicle-mounted communications device 204.

According to one example, the status indicator module 238 is configured to determine that the PPM 202 is communicatively coupled to the vehicle-mounted communications device 204. Accordingly, the processor of the PPM is configured to generate patient data further comprising the status indicator, where the status indicator indicates that the PPM 202 is communicatively coupled to the vehicle-mounted communications device 204.

According to another example, the status indicator module 238 is configured to determine that the PPM 202 is not communicatively coupled to the vehicle-mounted communications device 204. Accordingly, the processor of the PPM is configured to generate patient data further comprising the status indicator, where the status indicator indicates that the PPM 202 is not communicatively coupled to the vehicle-mounted communications device 204.

In the preceding examples, where a PPM is communicatively coupled to a vehicle-mounted communications device via a USB connection, a respective USB controller of the PPM and/or vehicle-mounted communications device may be arranged to detect whether or not the devices are communicatively coupled.

Each vehicle 106a, 106b may be associated with one or more PPMs 102a, 102b, 202. Each PPM may be substantially the same, or they may be different, for example by including more or fewer medical sensors 206a, 206b, and capabilities. In one example, a vehicle 106a includes two kinds of PPMs; a PPM 302, and a second PPM 402 (shown in FIG. 3). The second kind of PPM 402 may be a second kind of medical apparatus, for example.

Figure 3:
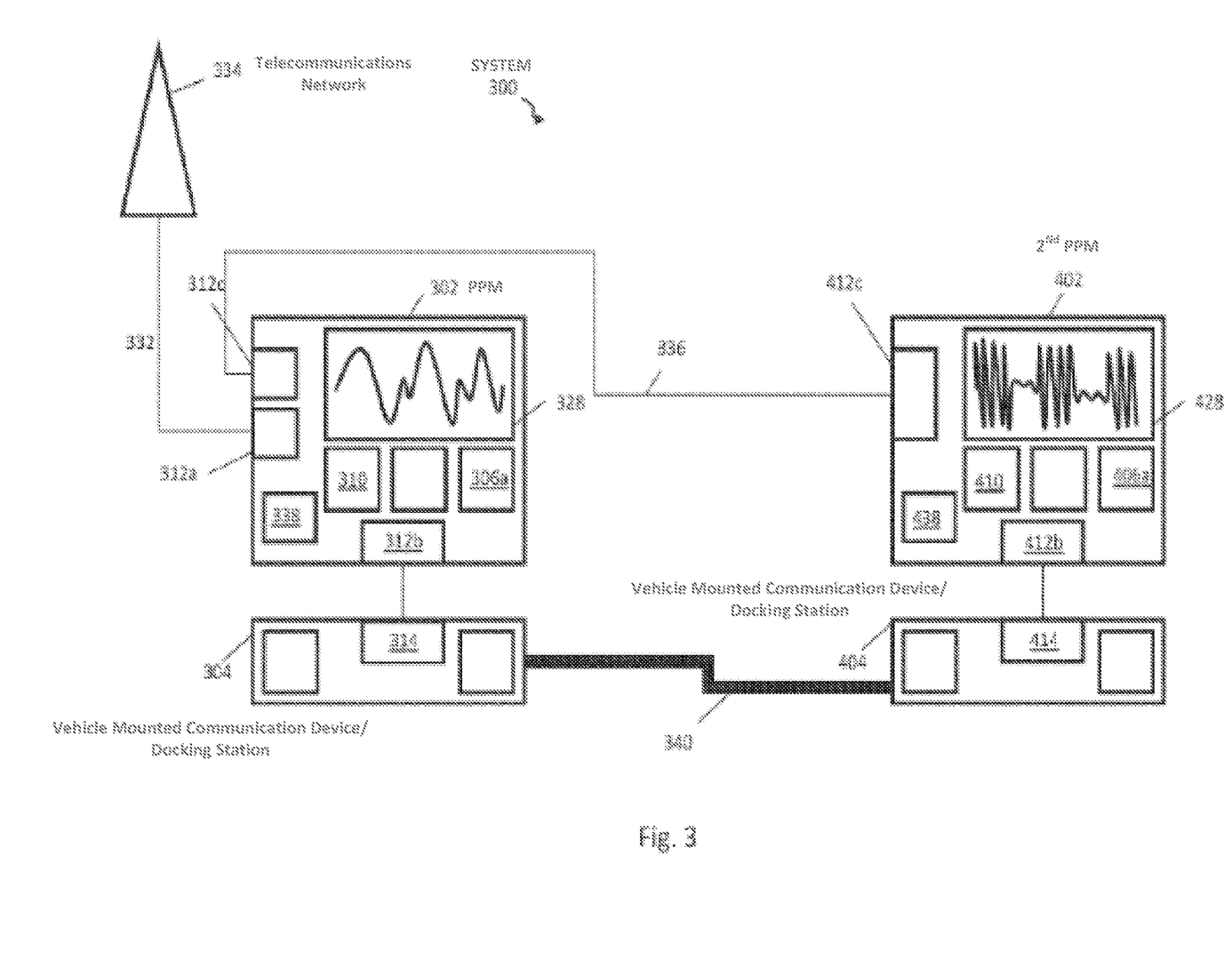
FIG. 3 is a block diagram of an example apparatus and vehicle mounted communications device, and an example second apparatus and second vehicle mounted communications device.

FIG. 3 depicts the PPM 302 and a second PPM 402 as part of a system 300. In this example, PPM 302 is different to the second PPM 402. Different can mean that any number of features can be different, for example they may include a different type and number of communication interfaces, be a different size, or include different medical sensors. In one example, the second kind of PPM 402 is a defibrillator. FIG. 3 depicts two kinds of PPMs, either or both of which may be identical or different to PPMs 102a, 102b, 202. The PPMs 302, 402 may include a battery 222 and buttons 223 for example.

The PPM 302 will be herein referred to as the "first" PPM 302. As in FIGS. 1 and 2, each PPM 302, 402 may be associated with a respective vehicle-mounted communications device 304, 404. The first PPM 302 may be communicatively coupleable to a first vehicle-mounted communications device 304 via communication interfaces 312b and 314. The second PPM 304 may be communicatively coupleable to a second vehicle-mounted communications device 404 via communication interfaces 412b and 414. One, or both vehicle-mounted communications devices 304, 404 may be identical to the vehicle-mounted communications device 204.

Furthermore, the first PPM 302 and the second PPM 402 may also be communicatively coupleable to each other via communication interfaces 312c and 412c. For example, the two PPMs 302, 402 may be communicatively coupled via a wireless connection (for example via Bluetooth) via communication path 336. To be connected this way, the first PPM 302 and second PPM 402 may first need to be "paired" before establishing the communication path 336 along which data may be transferred in either direction. This communication path 336 may be useful if one of the devices, for example the second PPM 402, lacks the capability to transmit data to the remote server 112. For example, the second PPM 402 may be a "satellite" PPM, connected to the first PPM 302, which relays data back to the first PPM 302 before the first PPM 302 transmits the data to the remote server 112 via communication interface 312a and communication path 332. However, in other examples both the first and second PPM 302, 402 have such capability.

In one example, the first vehicle-mounted communications device 304 and the second vehicle-mounted communications device 404 both comprise docking stations. The two docking stations may be formed as a single unit, into which each PPM may be docked, or may be formed as separate units, which are, for example, connected via one or more wired or wireless connections.

As mentioned above, data may be transmitted between the first PPM 302 and the second PPM 402 via a wireless communication path/channel 336. Having two PPMs 302, 402 means that care and treatment provided to a patient can be improved, and maintaining the communication path 336 between them allows each PPM 302, 402 to be used more effectively. Establishing this data connection (or communications channel) therefore needs to be performed efficiently—time should not be wasted on pairing and establishing the data connection manually in times of emergency. Typically a device needs to be paired with another device before a data connection can be established and maintained. Pairing is sometimes known as bonding, and is the process of setting up a data link between two devices to allow communications between them. An example communications channel may be established via Bluetooth, however "pairing" can refer to any other suitable protocol used to transmit data between devices.

An example herein provides efficient establishment of the wireless communications channel 336 using an "auto-pair" feature, which automatically pairs the first PPM 302 with the second PPM 402 when both are coupled via a communication path 340 (which in this example comprises one or more physical wires).

In some examples the first and second PPMs 302, 402 are coupled to one another via their respective docking stations 304, 404; the first docking station 304 being communicatively coupled to the second docking station 404 via the communication path 340. For example, the coupling between the first and second PPMs, via the respective docking stations, may comprise a USB connection. In other examples, the docking stations 304, 404 are not necessary and the first PPM 302 may be directly communicatively coupleable to the second PPM 402 via communication interfaces 312b and 412b, for example via a physical cable, such as a USB cable. In another example, the first and second docking stations 304, 404 are comprised within a single unit which is adapted to support the first and second PPMs 302, 402 and the first and second PPMs are communicatively coupled via an appropriate communications connection, such as a USB cable. The single unit may comprise the same features as vehicle mounted communications device 204, for example.

Regardless of how the first PPM 302 is physically-coupled with the second PPM 402, one of the PPMs 302, 304 may initiate the auto-pair procedure. In the following example, the first PPM 302 initiates the procedure, but it will be appreciated that this could be initiated by the second PPM 402.

According to one example, the first PPM 302 may detect that it is coupled to the second PPM 402 (either directly, or via the docking stations 304, 404). For example, the processor 310 or a status indicator module 338 (which may be the same as, and include the functionality of status indicator module 238), may detect or determine that the first PPM 302 is coupled to the second PPM 402. Accordingly, the first PPM 302 may perform a check to determine whether the PPM 302 and PPM 402 have previously been "paired". If they have, the PPM 302 may be configured to establish the wireless communication channel 336, otherwise the PPM 302 may be configured to first pair with the PPM 402 before establishing the wireless communication channel 336.

To pair the first PPM 302 with the second PPM 402, the first PPM 302 may itself initiate a pairing procedure and also cause the second PPM 402 to initiate a pairing procedure. Causing the second PPM 402 to initiate a pairing procedure may comprise transmitting an instruction/command via the communication path 340. Upon receipt of this instruction, the second PPM 402 may initiate the pairing procedure. When both PPMs 302, 402 have initiated the pairing procedure, the PPM 302 may discover the second PPM 402 and begin pairing. In one example, pairing may comprise entering a PIN. This PIN can be exchanged automatically via the communication path 340, for example. The first PPM 302 may therefore be paired with the second PPM 402. Once paired, the communication path 336 can be established to allow the transmission of data.

The auto-pair feature therefore allows two previously unpaired PPMs to be paired with reduced or no human intervention. Medical personnel may then use the PPMs 302, 402 knowing that they have been automatically paired and that the communication path 336 has been established to allow data to be transferred. This obviates the need for the user(s) to connect the two PPMs 302, 402 manually using current cumbersome connection procedures, and instead allows them to attend to a patient's needs more immediately.

In some examples, user input may be required to confirm that the pairing is allowed to occur. While this does require some human intervention, it is considerably less than is required during conventional pairing procedures. This user input may act as a safety feature, in case a user may wish to prevent the automatic pairing.

As mentioned, in certain examples, the auto-pair feature may be configured to initiate when the first docking station 304 is communicatively coupled to the second docking station 404 and the first PPM 302 is docked in the first docking station 304 and the second PPM 402 is docked in the second docking station 404. Accordingly, the first PPM 302 may be configured to pair with the second PPM 402 in response to detecting that the first PPM 302 is docked and that the second PPM 402 is docked. Again, this may be detected by the processor of the first PPM 302, or by the status indicator module 338. In this way, whenever one or both of the first and second PPMs 302, 402 are removed from their respective docking stations 304, 404 the devices are already paired, and the communication path 336 has been established, whereby data may be transferred wirelessly between the two PPMs.

In some examples, the communicative coupling 340 between the first docking station 304 and the second docking station 404 is a wireless communication.

System 300 therefore provides a quick and efficient method of automatically pairing two devices.

Figure 4:
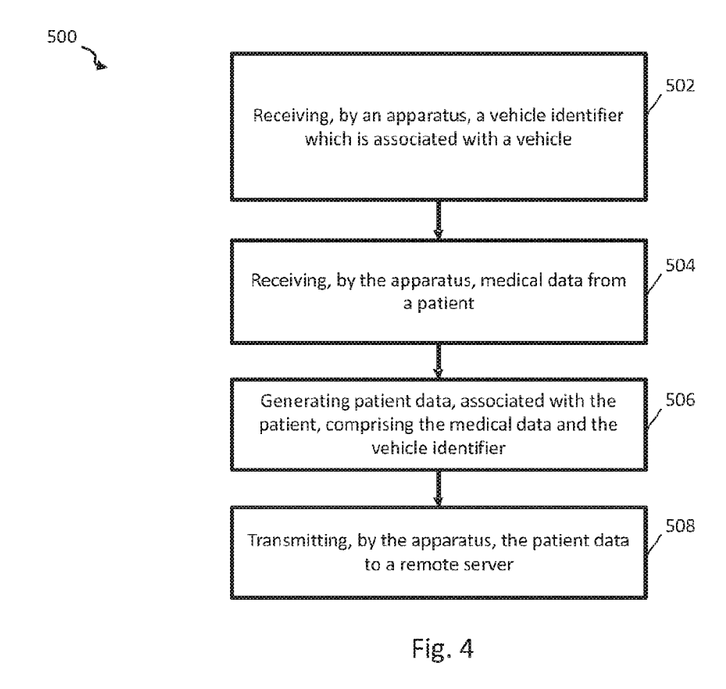
FIG. 4 is a flow diagram of a method used by the example apparatus to transmit a vehicle identifier to a remote server.

FIG. 4 is a flow diagram showing a method 500. The method 500 can be performed by any of the apparatus (PPMs) 102a, 102b, 202, and 302 discussed in FIGS. 1-3. At block 502 the method comprises receiving, by an apparatus, a vehicle identifier which is associated with a vehicle. At block 504 the method comprises receiving, by the apparatus, medical data relating to or received from a patient. At block 506, the method comprises generating patient data, associated with the patient, where the patient data comprises the medical data and the vehicle identifier. At block 508 the method comprises transmitting, by the apparatus, the patient data to a remote server. Using this method, the apparatus can transmit this to the remote server 112.

Additional, optional steps may also be included in the method and are described below. For example, block 502 may comprise the apparatus receiving the vehicle identifier from a vehicle mounted communications device.

The method may further comprise transmitting, by the apparatus to the vehicle-mounted communications device, the vehicle identifier. This can be used in some instances if the vehicle-mounted communications device is not already associated with a vehicle identifier.

The method may further comprise detecting, by the apparatus, that the vehicle-mounted communications device is not configured with a vehicle identifier and responsively transmitting, by the apparatus to the vehicle-mounted communications device, the vehicle identifier.

The method may further comprise detecting, by the apparatus, input from a user and responsively transmitting, by the apparatus to the vehicle-mounted communications device, the vehicle identifier.

The method may further comprise arranging, by the apparatus, the patient data into one or more data packets. Hence, block 506 would comprise transmitting the one or more data packets to the remote server.

The method may further comprise receiving, by the apparatus a second vehicle identifier which associated with a second vehicle. Hence, when the apparatus is moved into a different vehicle, the apparatus can obtain that vehicle's identifier.

The method may further comprise identifying, by the apparatus, which vehicle identifier is a current vehicle identifier.

The method may further comprise associating newly-received medical data with the current vehicle identifier.

The method may further comprise generating patient data comprising the medical data, the vehicle identifier and a patient identifier, arranging the patient data into one or more data packets, and transmitting the data packets to the remote server.

In some example methods, the vehicle-mounted communications device comprises a docking station which is adapted to receive the apparatus. The docking station may be communicatively coupled to a second docking station which is adapted to receive a second kind of medical apparatus. The method may further comprise detecting that the apparatus is communicatively coupled to the second kind of medical apparatus when the apparatus is docked in the docking station and the second kind of medical apparatus is docked in the second docking station, and establishing a wireless communications channel between the apparatus and the second kind of apparatus. In one example to establish a wireless communications channel comprises automatically pairing the devices and setting up a wireless communications channel.

The method may further comprise receiving, by the remote server, the patient data from the apparatus.

The method may further comprise obtaining, by the remote server, location information associated with the vehicle, using the vehicle identifier. For example, this may be obtained from the vehicle tracking system 122. The method may further comprise transmitting to a medical facility, by the remote server, data associated with the location information and the medical data.

The method may further comprise generating patient data comprising the medical data, the vehicle identifier and a status indicator, wherein the status indicator indicates whether the apparatus is communicatively coupled to the vehicle mounted communications device.

Certain system components and methods described herein may be implemented by way of non-transitory computer program code that is storable on a non-transitory storage medium. In some examples, the apparatus (PPMs) 102a, 102b, 202, 302 may comprise a non-transitory computer readable storage medium 208, comprising a set of computer-readable instructions stored thereon. The apparatus (PPMs) 102a, 102b, 202, 302 may further comprise at least one processor 210.

Figure 5:
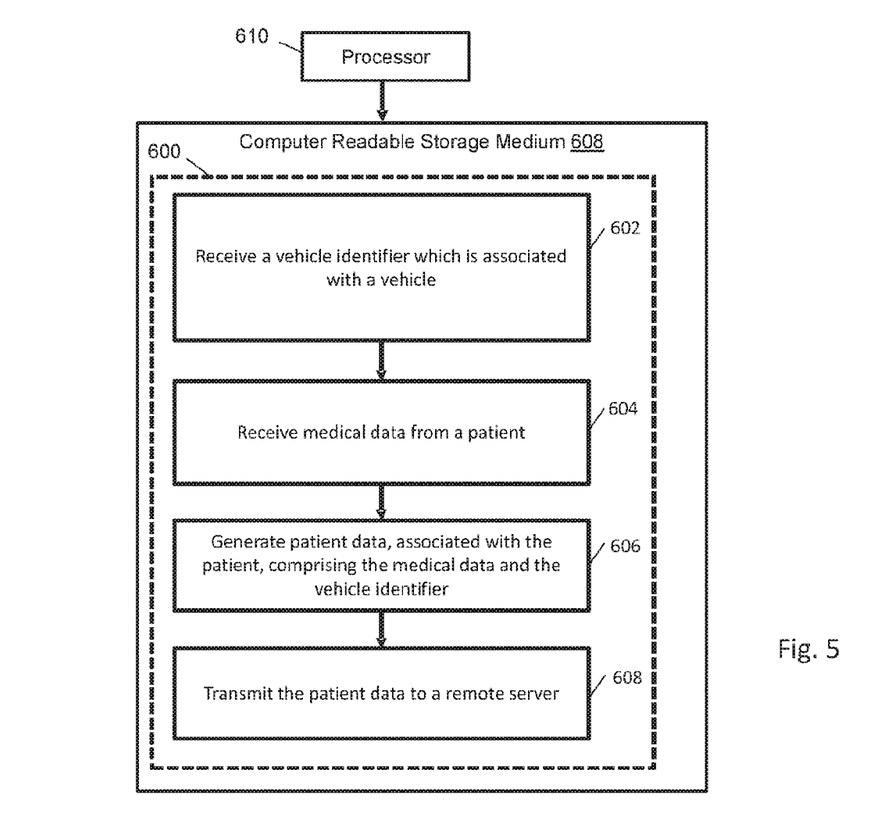
FIG. 5 is a block diagram of an example set of computer-readable instructions within a non-transitory computer-readable storage medium.

FIG. 5 shows an example of such a non-transitory computer-readable storage medium 608 comprising a set of computer readable instructions 600 which, when executed by at least one processor 610, cause the processor 610 to perform a method according to examples described herein. The computer readable instructions 600 may be retrieved from a machine-readable media, e.g. any media that can contain, store, or maintain programs and data for use by or in connection with an instruction execution system. In this case, machine-readable media can comprise any one of many physical media such as, for example, electronic, magnetic, optical, electromagnetic, or semiconductor media. More specific examples of suitable machine-readable media include, but are not limited to, a hard drive, a random-access memory (RAM), a read-only memory (ROM), an erasable programmable read-only memory, or a portable disc.

In an example, instructions 600 executed by the processor 610 cause an apparatus to, at block 602, receive a vehicle identifier which associated with a vehicle. At block 604 the instructions 600 executed by the processor 610 cause the apparatus to receive medical data relating to or received from a patient. At block 606 the instructions 600 executed by the processor 610 cause the apparatus to generate patient data, associated with the patient, comprising the medical data and the vehicle identifier. At block 608 the instructions 600 executed by the processor 610 cause the apparatus to transmit the patient data to a remote server. Further instructions not shown in FIG. 6 include the additional, optional steps discussed above.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A portable patient monitor for medically monitoring a patient, the portable patient monitor comprising:
   at least one medical sensor to receive medical data relating to or received from a patient being monitored;
   memory to store the received medical data and a received vehicle identifier, which is associated with a vehicle;
   a communications module; and
   a processor configured to:
      control the communications module to receive the vehicle identifier from a vehicle mounted communications device;
      generate patient data, associated with the patient being monitored, including the medical data and the vehicle identifier; and
      control the communications module to transmit the patient data to a remote server;
   wherein the vehicle mounted communications device includes a docking station and the portable patient monitor is adapted to be mounted in the docking station;
   wherein the docking station is configured to be communicatively coupled to a second docking station, which is adapted to receive a second kind of medical portable patient monitor; and
   wherein, responsive to when the portable patient monitor is docked in the docking station and to when the second kind of portable patient monitor is docked in the second docking station, the processor is further configured to establish a wireless communications channel between the portable patient monitor and the second kind of portable patient monitor.

2. The portable patient monitor of claim 1, wherein the processor is configured in a first mode to control the communications module to receive the vehicle identifier from the vehicle mounted communications device in response to:
   the portable patient monitor being moved into the vehicle from a second vehicle; and
   the portable patient monitor being communicatively coupled to the vehicle mounted communications device.

3. The portable patient monitor of claim 2, wherein the processor is further configured in a second mode to control the communications module to transmit a stored vehicle identifier to the vehicle-mounted communications device.

4. The portable patient monitor of claim 3, wherein the processor is further configured to operate the portable patient monitor in the second mode upon detection that the vehicle-mounted communications device is not configured with the stored vehicle identifier.

5. The portable patient monitor of claim 3, wherein the processor is further configured to operate the portable patient monitor in the second mode upon detection of an input from a user.

6. The portable patient monitor of claim 1, wherein the processor is configured to:
   arrange the patient data into one or more data packets; and
   control the communications module to transmit the data packets to the remote server.

7. The portable patient monitor of claim 1, wherein the processor is configured to:
   control the communication module to receive a second vehicle identifier, which is associated with a second vehicle; and
   store the second vehicle identifier in the memory.

8. The portable patient monitor of claim 7, wherein the processor is configured to identify in memory which vehicle identifier is a current vehicle identifier.

9. The portable patient monitor of claim 8, wherein the processor is configured to associate newly-received medical data with the current vehicle identifier.

10. The portable patient monitor of claim 1, wherein the processor is configured to:
   generate the patient data including the medical data, the vehicle identifier and a patient identifier;
   arrange the patient data into one or more data packets; and
   control the communications module to transmit the data packets to the remote server.

11. The portable patient monitor of claim 1, wherein the communications module includes a wireless telecommunications device to transmit the patient data to the remote server via a telecommunications network.

12. The portable patient monitor of claim 1, wherein the communications module includes a wired interface to receive the vehicle identifier from the vehicle-mounted communications device.

13. The portable patient monitor of claim 1, wherein the processor is configured to:
   generate the patient data including the medical data, the vehicle identifier and a status indicator, wherein the status indicator indicates whether the portable patient monitor is communicatively coupled to the vehicle mounted communications device.

14. A system for medically monitoring a patient, the system comprising:
   a portable patient monitor;
   a vehicle-mounted communications device including
      memory to store a vehicle identifier which is associated with a vehicle,
      a communications module to transmit the vehicle identifier to the portable patient monitor, and
      a docking station, wherein the portable patient monitor is adapted to be mounted in the docking station;
   wherein the portable patient monitor includes:
      at least one medical sensor to receive medical data relating to or received from a patient;

memory to store the received medical data and the vehicle identifier;
a communications module; and
a processor, configured to:
control the communications module of the portable patient monitor to receive the vehicle identifier from the vehicle-mounted communications device;
generate patient data, associated with the patient being monitored, including the medical data and the vehicle identifier; and
control the communication module of the portable patient monitor to transmit the patient data to a remote server; and
wherein, responsive to when the portable patient monitor is docked in the docking station and to when a second kind of portable patient monitor is docked in a second docking station communicatively coupled to the docking station, the processor is further configured to establish a wireless communications channel between the portable patient monitor and the second kind of portable patient monitor.

15. The system of claim 14, further comprising:
the remote server, wherein the remote server is configured to receive the patient data from the portable patient monitor.

16. The system of claim 15, wherein the remote server is configured to obtain, using the vehicle identifier, location information associated with the vehicle.

17. The system of claim 16, wherein data, associated with the location information and the received medical data, is sent by the remote server, to a medical facility.

18. A method for medically monitoring a patient by a system including a portable patient monitor and a vehicle-mounted communications device having a docking station, the method comprising:
receiving, by the portable patient monitor from the vehicle-mounted communications device, a vehicle identifier which is associated with a vehicle;
receiving, by the portable patient monitor, medical data relating to or received from a patient;
generating, by the portable patient monitor, patient data associated with the patient, including the medical data and the vehicle identifier;
transmitting, by the portable patient monitor, the patient data to a remote server; and
detecting when the portable patient monitor is communicatively coupled to a second kind of medical portable patient monitor when the portable patient monitor is docked in the docking station and the second kind of medical portable patient monitor is docked in a second docking station; and
establishing a wireless communications channel between the portable patient monitor and the second kind of portable patient monitor based on the detecting when the portable patient monitor is communicatively coupled to the second kind of medical portable patient monitor.

19. The method of claim 18, further comprising:
transmitting, by the portable patient monitor to the vehicle-mounted communications device, a stored vehicle identifier.

20. The method of claim 19, further comprising:
detecting, by the portable patient monitor, input from a user; and
responsively transmitting to the input from the user, by the portable patient monitor to the vehicle-mounted communications device, a stored vehicle identifier.

21. The method of claim 18, further comprising:
detecting, by the portable patient monitor, that the vehicle-mounted communications device is not configured with a stored vehicle identifier; and
responsively transmitting, by the portable patient monitor to the vehicle-mounted communications device, the stored vehicle identifier.

22. The method of claim 18, further comprising:
arranging, by the portable patient monitor, the patient data into one or more data packets, wherein transmitting, by the portable patient monitor, the patient data to the remote server includes transmitting the one or more data packets to the remote server.

23. The method of claim 18, further comprising:
receiving, by the portable patient monitor, a second vehicle identifier which is associated with a second vehicle.

24. The method of claim 23, further comprising identifying, by the portable patient monitor, which vehicle identifier is a current vehicle identifier.

25. The method of claim 24, further comprising associating newly-received medical data with the current vehicle identifier.

26. The method of claim 18, further comprising:
generating, by the portable patient monitor, the patient data including the medical data, the vehicle identifier and a patient identifier;
arranging, by the portable patient monitor, the patient data into one or more data packets; and
transmitting, by the portable patient monitor, the data packets to the remote server.

27. The method of claim 18, further comprising receiving, by the remote server, the patient data from the portable patient monitor.

28. The method of claim 18, further comprising obtaining, by the remote server, location information associated with the vehicle, using the vehicle identifier.

29. The method of claim 28, further comprising transmitting to a medical facility, by the remote server, data associated with the location information and the medical data.

30. The method of claim 18, further comprising:
generating, by the portable patient monitor, the patient data including the medical data, the vehicle identifier and a status indicator, wherein the status indicator indicates whether the portable patient monitor is communicatively coupled to the vehicle mounted communications device.

31. A non-transitory computer readable storage medium comprising a set of computer-readable instructions stored thereon, which, when executed by a processor, cause the processor to, implement a method for medically monitoring a patient by a system including a portable patient monitor and a vehicle-mounted communication device having a docking station, the method comprising:
receiving, by the portable patient monitor from the vehicle-mounted communications device, a vehicle identifier which is associated with a vehicle;
receiving, by the portable patient monitor, medical data relating to or received from a patient;
generating, by the portable patient monitor, patient data associated with the patient, including the medical data and the vehicle identifier;
transmitting, by the portable patient monitor, the patient data to a remote server; and detecting when the portable patient monitor is communicatively coupled to a second kind of medical portable patient monitor when the portable patient monitor is docked in the docking station and the second kind of medical portable patient monitor is docked in a second docking station; and establishing a wireless communications channel between the portable patient monitor and the second kind of portable patient monitor based on the detecting when the portable patient monitor is communicatively coupled to the second kind of medical portable patient monitor.

\* \* \* \* \*